United States Patent
Shen et al.

(10) Patent No.: US 10,004,447 B2
(45) Date of Patent: *Jun. 26, 2018

(54) SYSTEMS AND METHODS FOR COLLECTING AND DISPLAYING USER ORIENTATION INFORMATION ON A USER-WORN SENSOR DEVICE

(71) Applicant: Leaf Healthcare, Inc., Pleasanton, CA (US)

(72) Inventors: Daniel Z. Shen, Stanford, CA (US); Barrett J. Larson, Palo Alto, CA (US); Mark V. Weckwerth, Pleasanton, CA (US)

(73) Assignee: LEAF HEALTHCARE, INC., Pleasanton, CA (US)

( * ) Notice: Subject to any disclaimer, the term of this patent is extended or adjusted under 35 U.S.C. 154(b) by 0 days. days.

This patent is subject to a terminal disclaimer.

(21) Appl. No.: 15/487,663

(22) Filed: Apr. 14, 2017

(65) Prior Publication Data

US 2017/0245793 A1     Aug. 31, 2017

Related U.S. Application Data

(63) Continuation of application No. 15/028,018, filed as application No. PCT/US2014/059756 on Oct. 8, (Continued)

(51) Int. Cl.
| | |
|---|---|
| G08B 5/22 | (2006.01) |
| A61B 5/00 | (2006.01) |
| A61B 5/11 | (2006.01) |

(52) U.S. Cl.
CPC ........... *A61B 5/447* (2013.01); *A61B 5/0015* (2013.01); *A61B 5/0077* (2013.01); (Continued)

(58) Field of Classification Search
None
See application file for complete search history.

(56) References Cited

U.S. PATENT DOCUMENTS

| 4,055,168 A | 10/1977 | Miller et al. | ................... 600/594 |
| 5,038,137 A | 8/1991 | Lloyd | ......................... 340/573.7 |

(Continued)

FOREIGN PATENT DOCUMENTS

| JP | 08238275 A | 9/1996 | ............... A61B 5/00 |
| JP | 11136191 A | 5/1999 | ............... A61B 5/00 |

(Continued)

OTHER PUBLICATIONS

Braden, Barbara et al., "Braden Scale—for Predicting Pressure Sore Risk," Form 3166P, 1 page, ©1988.
(Continued)

*Primary Examiner* — Brent Swarthout
(74) *Attorney, Agent, or Firm* — Slayden Grubert Beard PLLC

(57) ABSTRACT

A system for determining the location of patients uses a patient-associated communicator which wirelessly communicates with a network of environmental reference communicators arranged at fixed or otherwise known locations. A camera can be used to monitor or detect pressure ulcers and relay the information to a host system. Other embodiments are also disclosed.

12 Claims, 14 Drawing Sheets

Related U.S. Application Data 2014, now Pat. No. 9,655,546, application No. 15/487,663, which is a continuation-in-part of application No. 13/070,189, filed on Mar. 23, 2011, and a continuation-in-part of application No. 14/244,720, filed as application No. PCT/US2012/000488 on Oct. 3, 2012, application No. 15/487,663, which is a continuation-in-part of application No. 14/543,887, filed on Nov. 17, 2014, now Pat. No. 9,728,061.

(60) Provisional application No. 61/888,078, filed on Oct. 8, 2013, provisional application No. 61/905,106, filed on Nov. 15, 2013, provisional application No. 62/047,642, filed on Sep. 8, 2014, provisional application No. 61/438,732, filed on Feb. 2, 2011, provisional application No. 61/326,664, filed on Apr. 22, 2010, provisional application No. 61/411,647, filed on Nov. 9, 2010, provisional application No. 61/393,364, filed on Oct. 15, 2010, provisional application No. 61/373,260, filed on Aug. 12, 2010, provisional application No. 61/542,785, filed on Oct. 3, 2011.

(52) U.S. Cl.
CPC .......... *A61B 5/1114* (2013.01); *A61B 5/6801* (2013.01); *A61B 5/7275* (2013.01); *A61B 5/742* (2013.01)

(56) References Cited

U.S. PATENT DOCUMENTS

| | | | | |
|---|---|---|---|---|
| 5,146,206 | A | 9/1992 | Callaway | 340/573.7 |
| 5,300,921 | A | 4/1994 | Hoch et al. | 340/573.6 |
| 5,430,435 | A | 7/1995 | Hoch et al. | 340/573.7 |
| 5,519,380 | A | 5/1996 | Edwards | 340/573.4 |
| 5,588,437 | A | 12/1996 | Byrne et al. | 600/504 |
| 5,623,760 | A | 4/1997 | Newham | 29/622 |
| 5,669,377 | A | 9/1997 | Fenn | 128/200.24 |
| 5,769,784 | A | 6/1998 | Barnett et al. | 600/300 |
| 5,774,055 | A | 6/1998 | Pomerantz | 340/573.7 |
| 6,014,346 | A | 1/2000 | Malone | 368/10 |
| 6,030,351 | A | 2/2000 | Schmidt et al. | 600/592 |
| 6,129,686 | A | 10/2000 | Friedman | 600/595 |
| 6,287,253 | B1 | 9/2001 | Ortega et al. | 600/300 |
| 6,447,460 | B1 | 9/2002 | Zheng et al. | 600/549 |
| 7,007,327 | B2 | 3/2006 | Ogawa et al. | 5/609 |
| 7,090,647 | B2 | 8/2006 | Mimura et al. | 600/587 |
| 7,184,963 | B1 | 2/2007 | Shannon | 705/2 |
| 7,251,845 | B2 | 8/2007 | Schaller et al. | 5/613 |
| 7,325,453 | B2 | 2/2008 | Bremer et al. | 73/510 |
| 7,378,975 | B1 | 5/2008 | Smith et al. | 340/573.1 |
| 7,600,409 | B2 | 10/2009 | Ukai | 73/1.39 |
| 7,634,379 | B2 | 12/2009 | Noble | 702/141 |
| 7,698,830 | B2 | 4/2010 | Townsend et al. | 33/512 |
| 7,753,861 | B1 | 7/2010 | Kahn et al. | 600/595 |
| 8,237,551 | B2 | 8/2012 | Sweeney et al. | 340/286.07 |
| 8,306,666 | B2 | 11/2012 | Huber et al. | 700/275 |
| 8,436,737 | B1 | 5/2013 | Trout | 340/573.7 |
| 8,475,368 | B2 | 7/2013 | Tran et al. | 600/300 |
| 8,604,916 | B2 | 12/2013 | Mcneely et al. | 340/286.07 |
| 8,606,344 | B2 | 12/2013 | Dimaio et al. | 600/407 |
| 8,674,826 | B2 | 3/2014 | Becker et al. | 340/539.12 |
| 8,684,900 | B2 | 4/2014 | Tran | 600/3 |
| 8,781,504 | B1 | 7/2014 | Liu | 455/456.5 |
| 9,005,141 | B1 | 4/2015 | Najafi et al. | 600/595 |
| 9,141,974 | B2 | 9/2015 | Jones et al. | |
| 9,655,546 | B2 * | 5/2017 | Shen | G06F 19/3406 |
| 2001/0049609 | A1 | 12/2001 | Girouard et al. | 705/3 |
| 2003/0171954 | A1 | 9/2003 | Guerin et al. | 705/2 |
| 2004/0046668 | A1 | 3/2004 | Smith et al. | 340/573.7 |
| 2005/0033200 | A1 | 2/2005 | Soehren et al. | 600/595 |
| 2005/0172398 | A1 | 8/2005 | Smith et al. | 5/81.1 R |
| 2005/0256435 | A1 | 11/2005 | Hess | 602/2 |
| 2006/0001545 | A1 | 1/2006 | Wolf | 340/573.1 |
| 2006/0021240 | A1 | 2/2006 | Horgan | 33/366.11 |
| 2006/0089538 | A1 | 4/2006 | Cuddihy et al. | 600/300 |
| 2006/0116904 | A1 | 6/2006 | Brem | 705/2 |
| 2006/0270949 | A1 | 11/2006 | Mathie et al. | 600/595 |
| 2006/0279426 | A1 | 12/2006 | Bonnet et al. | 340/573.1 |
| 2007/0132597 | A1 | 6/2007 | Rodgers | 340/573.1 |
| 2007/0159332 | A1 | 7/2007 | Koblasz | 340/572.1 |
| 2008/0001735 | A1 | 1/2008 | Tran | 340/539.22 |
| 2008/0129518 | A1 | 6/2008 | Carlton-Foss | 340/573.1 |
| 2008/0272918 | A1 | 11/2008 | Ingersoll | 340/573.1 |
| 2008/0275349 | A1 | 11/2008 | Halperin et al. | 600/484 |
| 2009/0024065 | A1 | 1/2009 | Einarsson | 602/26 |
| 2009/0069642 | A1 | 3/2009 | Gao et al. | 600/300 |
| 2009/0099480 | A1 | 4/2009 | Salgo et al. | 600/595 |
| 2009/0119843 | A1 | 5/2009 | Rodgers et al. | 5/611 |
| 2009/0174565 | A1 * | 7/2009 | Chan | G08B 21/0446 340/669 |
| 2009/0185763 | A1 | 7/2009 | Park et al. | 382/311 |
| 2009/0237264 | A1 | 9/2009 | Bobey et al. | 340/815.69 |
| 2009/0254003 | A1 | 10/2009 | Buckman | 600/595 |
| 2009/0318908 | A1 | 12/2009 | Van Pieterson et al. | 606/9 |
| 2010/0010385 | A1 | 1/2010 | Skelton et al. | 600/595 |
| 2010/0081385 | A1 | 4/2010 | Lin et al. | 455/41.3 |
| 2010/0121227 | A1 | 5/2010 | Stirling et al. | 600/595 |
| 2010/0156653 | A1 | 6/2010 | Chaudhari et al. | 340/686.1 |
| 2010/0162832 | A1 | 7/2010 | Brauers | 73/862.626 |
| 2010/0231376 | A1 | 9/2010 | Hirose | 340/517 |
| 2010/0298742 | A1 * | 11/2010 | Perlman | A61B 5/1116 600/595 |
| 2011/0025493 | A1 | 2/2011 | Papadopoulos et al. | 340/539.12 |
| 2011/0050411 | A1 | 3/2011 | Schuman et al. | 340/539.13 |
| 2011/0066007 | A1 | 3/2011 | Banet et al. | 600/301 |
| 2011/0066009 | A1 | 3/2011 | Moon et al. | 600/301 |
| 2011/0082672 | A1 | 4/2011 | Hardigan | 703/2 |
| 2011/0084806 | A1 | 4/2011 | Perkins | 340/10.1 |
| 2011/0112442 | A1 | 5/2011 | Meger et al. | 600/595 |
| 2011/0156915 | A1 | 6/2011 | Brauers et al. | 340/573.4 |
| 2011/0201972 | A1 | 8/2011 | Ten Kate | 600/595 |
| 2011/0245732 | A1 | 10/2011 | Mravyan et al. | 600/587 |
| 2011/0263950 | A1 * | 10/2011 | Larson | A61B 5/1113 600/301 |
| 2012/0029392 | A1 | 2/2012 | Jin et al. | 600/595 |
| 2012/0101770 | A1 | 4/2012 | Grabiner et al. | 702/141 |
| 2012/0172685 | A1 | 7/2012 | Gilbert | 600/306 |
| 2012/0253142 | A1 | 10/2012 | Meger et al. | 600/301 |
| 2012/0253485 | A1 | 10/2012 | Weast et al. | 700/91 |
| 2012/0259577 | A1 * | 10/2012 | Ganyi | A61B 5/1117 702/139 |
| 2012/0277637 | A1 | 11/2012 | Vandatpour et al. | 600/595 |
| 2013/0006151 | A1 | 1/2013 | Main et al. | 600/587 |
| 2013/0090571 | A1 | 4/2013 | Nourani et al. | 600/587 |
| 2013/0096390 | A1 | 4/2013 | Weller-brophy et al. | 600/300 |
| 2013/0141233 | A1 | 6/2013 | Jacobs et al. | 340/521 |
| 2014/0188638 | A1 | 7/2014 | Jones et al. | 705/16 |
| 2014/0259414 | A1 | 9/2014 | Hayes et al. | 5/611 |
| 2015/0082542 | A1 | 3/2015 | Hayes et al. | 5/600 |
| 2015/0121261 | A1 | 4/2015 | Collado et al. | 715/764 |
| 2015/0136146 | A1 | 5/2015 | Hood et al. | 128/845 |
| 2015/0302539 | A1 * | 10/2015 | Mazar | G08B 21/0211 705/3 |
| 2015/0351981 | A1 | 12/2015 | Sazonov | 297/217.2 |

FOREIGN PATENT DOCUMENTS

| | | | | |
|---|---|---|---|---|
| JP | 2003116858 | A | 4/2003 | A61B 10/00 |
| JP | 2004121837 | A | 4/2004 | A47C 19/04 |
| JP | 2006122376 | A | 5/2006 | A61B 5/22 |
| JP | 2006175206 | A | 7/2006 | A61B 5/107 |
| JP | 2007040848 | A | 2/2007 | A61B 5/11 |
| JP | 2008027030 | A | 2/2008 | A61B 5/00 |
| JP | 2008295644 | A | 12/2008 | A47C 21/00 |
| JP | 2010022723 | A | 2/2010 | A61B 5/028 |
| JP | 2010035579 | A | 2/2010 | A61G 12/00 |
| JP | 2011183121 | A | 9/2011 | A61B 5/11 |
| WO | 03/079898 | A1 | 10/2003 | A61B 5/11 |
| WO | 2007/119070 | A1 | 10/2007 | A01K 11/00 |

(56) References Cited

FOREIGN PATENT DOCUMENTS

| WO | 2008/113556 A1 | 9/2008 | ............... A61B 5/11 |
|---|---|---|---|
| WO | 2010/105045 A2 | 9/2010 | ............... A61B 5/02 |
| WO | 2010/111363 A2 | 9/2010 | ............. A61B 5/103 |
| WO | 2011/087807 A2 | 7/2011 | ........... A61B 5/0059 |
| WO | 2012/037470 A1 | 3/2012 | ............. G01C 21/00 |
| WO | 2013/052123 A1 | 4/2013 | ............. A61B 5/103 |
| WO | 2013/109410 A1 | 7/2013 | ............ H04W 24/00 |
| WO | 2015/054423 A1 | 4/2015 | ............... A61B 5/11 |
| WO | 2015/074007 A1 | 5/2015 | ............... A61B 5/00 |

OTHER PUBLICATIONS

Halfens, R.J.G. et al., "Validity and Reliability of the Braden Scale and the Influence of other Risk Factors: A Multi-Centre Prospective Study," International Journal of Nursing Studies, vol. 37, pp. 313-319, Aug. 30, 1999.

Defloor, Torn, "The Effect of Position and Mattress on Interface Pressure," Applied Nursing Research, vol. 13, No. 1, pp. 2-11, Feb. 2000.

Keller, B.J. et al.,"Pressure Ulcers in Intensive Care Patients: A Review of Risks and Prevention," Intensive Care Med, vol. 28, pp. 1379-1388, Sep. 7, 2002.

Lyder, Courtney H. et al., "Chapter 12. Pressure Ulcers: A Patient Safety Issue," In *Patient Safety and Quality: An Evidence-Based Handbook for Nurses*, Agency for Research and Quality, 33 Pages, Apr. 2008.

Peterson, M. et al., "Effects of Elevating the Head of Bed on Interface Pressure in Volunteers," Critical Care Medicine, vol. 36, No. 11, pp. 3038-3042, Nov. 2008.

Ostadabbas, Sarah et al., "Pressure Ulcer Prevention: An Efficient Turning Schedule for Bed-Bound Patients," IEEE/NIH Life Science Systems and Applications Workshop, pp. 159-162, 2011.

Cox, Jill, "Predictors of Pressure Ulcers in Adult Critical Care Patients," American Journal of Critical Care, vol. 20, No. 5, pp. 364-374, Sep. 2011.

Dhillon, Marshal et al., "Towards the Prevention of Pressure Ulcers with a Wearable Patient Posture Monitor Based on Adaptive Accelerometer Alignment," 34th Annual International Conference of the IEEE EMBS San Diego, CA, pp. 4513-4516, Aug. 28, 2012.

U.S. Non-Final Office Action, U.S. Appl. No. 15/187,516, 42 pages, dated May 11, 2017.

U.S. Non-Final Office Action, U.S. Appl. No. 15/173,612, 38 pages, dated May 12, 2017.

European Invitation to Pay Additional Fees, Application No. 14862053.7, 13 pages, dated May 23, 2017.

International Search Report and Written Opinion, Application No. PCT/US2017/025832, 11 pages, dated Jun. 21, 2017.

U.S. Non-Final Office Action, U.S. Appl. No. 15/601,593, 31 pages, dated Aug. 15, 2017.

Invitation to Pay Additional Fees and Partial International Search Report, Application No. PCT/US2017/037589, 15 pages, dated Aug. 23, 2017.

Wang, Jue et al., "A Compound Sensor for Biomechanical Analyses of Buttock Soft Tissue in Vivo," Journal of Rehabilitation Research and Development, vol. 37, No. 4, pp. 433-443, Dec. 14, 1999.

Lowne, D.R., "Designing a Low-Cost Mattress Sensor for Automated Body Position Classification," IEEE Engineering in Medicine and Biology 27th Annual Conference, pp. 6437-6440, 2005.

DeFloor, Tom et al., "The Effect of Various Combinations of Turning and Pressure Reducing Devices on the Incidence of Pressure Ulcers," International Journal of Nursing Studies, vol. 42, No. 1, pp. 37-46, Jan. 2005.

Wai, A.A. et al., "Sleeping Patterns Observation for Bedsores and Bed-Side Falls Prevention," Annual International Conference of the IEEE Engineering in Medicine and Biology Society, pp. 6087-6090, 2009.

Hsia, C.C. et al., "Analysis and Comparison of Sleeping Posture Classification Methods using Pressure Sensitive Bed System," Annual International Conference of the IEEE Engineering in Medicine and Biology Society, pp. 6131-6134, Sep. 2009.

Yip, Marcus et al., "A Flexible Pressure Monitoring System for Pressure Ulcer Prevention," 31st Annual International Conference of the IEEE EMBS, Minneapolis, Minnesota, pp. 1212-1215, Sep. 2, 2009.

International Search Report and Written Opinion, Application No. PCT/US2012/00488, 6 pages, dated Jan. 23, 2013.

International Search Report and Written Opinion, Application No. PCT/US2014/066016, 6 pages, dated Feb. 11, 2015.

U.S. Non-Final Office Action, U.S. Appl. No. 15/028,018, 22 pages, dated Nov. 14, 2016.

U.S. Final Office Action, U.S. Appl. No. 14/244,720, 39 pages, dated Dec. 1, 2016.

Japanese Office Action, Application No. 2012557312, 9 pages, dated Jan. 10, 2017.

U.S. Non-Final Office Action, U.S. Appl. No. 15/036,782, 28 pages, dated Mar. 29, 2017.

U.S. Non-Final Office Action, U.S. Appl. No. 14/244,720, 39 pages, dated Apr. 19, 2017.

International Search Report and Written Opinion, Application No. PCT/US2017/037589, 19 pages, dated Oct. 16, 2017.

U.S. Final Office Action, U.S. Appl. No. 15/173,612, 51 pages, dated Nov. 14, 2017.

European Partial Supplementary Search Report, Application No. 14851948.1, 17 pages, dated Jun. 8, 2017.

European Extended Search Report, Application No. 14862053.7, 11 pages, dated Sep. 7, 2017.

European Extended Search Report, Application No. 14851948.1, 13 pages, dated Sep. 19, 2017.

Japanese Office Action, Application No. 2016530839, 6 pages, dated Dec. 12, 2017.

U.S. Non-Final Office Action, U.S. Appl. No. 15/696,908, 28 pages, dated Dec. 22, 2017.

International Search Report and Written Opinion, Application No. PCT/US2017/038511, 12 pages, dated Oct. 5, 2017.

Kraft, Peter et al., "Christmas 2009: Young and Old: Lying Obligquely—A Clinical Sign of Cognitive Impairment: Cross Sectional Obersvational Study," BMJ, vol. 339, 5 pages, dated Nov. 17, 2009.

European Extended Search Report, Application No. 17204228.5, 6 pages, dated Mar. 28, 2018.

U.S. Non-Final Office Action, U.S. Appl. No. 15/654,928, 47 pages, dated Jan. 25, 2018.

\* cited by examiner

ENVIRONMENTAL REFERENCE COMMUNICATOR

SYSTEMS AND METHODS FOR COLLECTING AND DISPLAYING USER ORIENTATION INFORMATION ON A USER-WORN SENSOR DEVICE

CROSS-REFERENCE TO RELATED APPLICATIONS

This application is:

(a) a continuation of U.S. Non-Provisional patent application Ser. No. 15/028,018, now U.S. Pat. No. 9,655,546, filed on Apr. 7, 2016, which claims the benefit under 35 U.S.C. § 371 of PCT/US2014/59756 filed October 8, 2014, which claims the benefit of the following U.S. Provisional Applications: (i) Ser. No. 61,888,078 filed Oct. 8, 2013, (ii) Ser. No. 61/905,106 filed Nov. 15, 2013, and (iii) Ser. No. 62/047,642 filed Sep. 8, 2014; and (b) a continuation-in-part of each of the following applications:
  (1) co-pending U.S. Non-Provisional patent application Ser. No. 13/070, 189 filed Mar. 23, 2011, which claims the benefit of the following U.S. Provisional Applications: (i) Ser. No. 61/438,732 filed Feb. 2, 2011, (ii) Ser. No. 61/326,664 filed Apr. 22, 2010, (iii) Ser. No. 61/411,647 filed Nov. 9, 2010, (iv) Ser. No. 61/393,364 filed Oct. 15, 2010, and (v) Ser. No. 61/373,260 filed Aug. 12, 2010,
  (2) co-pending U.S. Non-Provisional patent application Ser. No. 14/244,720 filed Apr. 3, 2014, which claims the benefit under 35 U.S.C. § 371 of PCT/US2012/000488 filed Oct. 3, 2012, which claims the benefit of U.S. Provisional Application Ser. No. 61/542,785 filed Oct. 3,2011, and
  (3) U.S. Non-Provisional patent application Ser. No. 14/543,887, now U.S. Pat. No. 9,728,061, filed Nov. 17, 2014, which claims the benefit of the following U.S. Provisional Applications: (i) Ser. No. 61/905,106 filed Nov. 15, 2013, and (ii) Ser. No. 62/047,642 filed Sep. 8, 2014.

The present application claims the benefit of each application listed above, and the entire contents of each application listed above are incorporated herein by reference.

FIELD OF THE INVENTION

Aspects of the present invention relate generally to systems, devices and methods for the detection of compromised tissue perfusion and other issues affecting the health of a patient, and more particularly relates to systems, devices and methods for such detection, communicating of relevant information to a host, and providing either appropriate guidance to a caregiver to facilitate proper management of the patient or device instructions for providing automated care.

BACKGROUND OF THE INVENTION

Management of pressure ulcers and other health conditions poses a substantial burden to the healthcare system. Each year, the United States spends billions of dollars treating pressure ulcers and associated complications. Pressure ulcers are very common and they represent a significant source of morbidity and mortality for patients. The prevalence of pressure ulcers in the US alone is estimated to be between 1.5 and 3.0 million people, with two thirds of cases involving patients 70 or older.

Pressure ulcers, which are also known as pressure sores, bed sores, or decubitus ulcers, represent localized areas of tissue damage. Pressure ulcers often occur when the soft tissue between a bony prominence and an external surface is compressed for an extended period of time. Pressure ulcers can also occur from friction, such as by rubbing against a bed, cast, brace, or the like. Pressure ulcers commonly occur in immobilized patients who are confined to a bed, chair or wheelchair. Localized tissue ulceration results when pressure on the skin exceeds capillary filling pressure (approximately 32 mm Hg), which thereby impedes the microcirculation in the skin and the underlying subcutaneous tissue. With compromised blood flow, the delivery of oxygen and nutrients to target tissues is impaired. If blood flow is not restored promptly, the skin and subcutaneous tissue will die and a pressure ulcer will develop.

Pressure ulcers will initially appear as areas of red or pink skin discoloration, but these areas can quickly develop into open wounds if left untreated. Open wounds can lead to severe health complications by exposing patients to life-threatening infections. The primary goal in the treatment and prevention of pressure ulcers is to relieve pressure on and around affected tissues. Pressure relief can be accomplished by frequently changing the position of immobilized patients and by using support surfaces that minimize surface pressure. Although pressure management is the most critical aspect of any successful treatment program, it is also important to ensure that patients receive adequate nutrition, engage in daily exercise, and follow a good skin care and personal hygiene protocol.

Various devices and methods for treating and preventing pressure ulcers have been developed. The cornerstone of pressure ulcer prevention is to turn patients on a regular basis, such as every one or two hours. Patients confined to a wheelchair, chair, or other surface should be moved in such a manner. Intermittent relief of surface pressure has proven to be highly effective in preventing the development of pressure ulcers. However, various factors limit compliance with turning/repositioning protocols.

There is a long-felt, definite and even urgent need for a system, method, and device that helps to prevent, detect, and/or treat pressure-induced ischemia and pressure ulcers by optimizing surface pressure at areas of compromised tissue perfusion. Various aspects of the present invention accomplish these objectives and substantially depart from the conventional concepts and designs of the prior art.

SUMMARY OF THE INVENTION

The present invention provides, in various aspects, a more accurate means for determining the location of patients with respect to a care environment. In an embodiment, a patient-associated communicator ("PAC") is capable of sending and/or receiving wireless signals and determining its orientation relative to a patient and/or the environment. A plurality of environmental reference communicators (ERCs) are distributed at fixed or known reference locations. The PACs communicate with one or more ERCs, permitting a specific PAC location to be determined. In various embodiments, the PACs can be affixed to the patient, or can be a beacon or other device affixed to a patient bed. In some embodiments the PACs have indicia so that a user such as a caregiver can easily orient the sensor with respect to the patient.

In another aspect, a camera in communication with either the PACs or the ERCs is used to visually document the presence, absence, current condition, or progression of pressure ulcers for a monitored patient. That data is logged and stored for appropriate analysis. Image standardization can be provided to permit visual data obtained from a camera to be standardized to, for example, improve documentation. Image characteristics that may need to be standardized include image orientation, viewing angle, viewing distance, brightness, color, etc. To assist in image standardization, a visual reference may be placed within the field of the image.

To assist in monitoring patient position, PACs can, in some embodiments, include indicators such as LEDs that can indicate which side the patient is on, when a patient requires a turn, which area of the body has been exposed to the most pressure, which direction a patient should be turned onto, or when a patient has been turned sufficiently to satisfy a turning protocol or to depressurize a given area.

In another aspect of the invention, patient self-roll or repositioning can be encouraged by various means, such as audio, visual or physical/tactile guidance. In a related aspect, acceleration and orientation monitoring of the patient may be used to monitor for motion caused by an alternating pressure mattress. The monitoring system of the present invention, by detecting patient accelerations, can determine if a patient is being repositioned sufficiently. In some embodiments, the system can include a pressure measurement system which can produce a pressure map of reasonable precision that then feeds back to a support surface.

In yet another aspect, patients who are immobilized for long periods of time often require prophylaxis to prevent against deep venous thrombosis (DVT). Patients considered at risk for DVTs will generally receive DVT prophylaxis, which can be pharmacologic or mechanical in nature.

In another aspect, the system can automatically calculate at least one suggested decompression threshold/interval. The decompression threshold/interval refers to the minimum amount of time that an area of the body needs to experience reduced pressure or no pressure in order to adequately re-profuse that area of the body, thereby preventing ischemia and tissue damage. In a further related aspect, the present invention can also detect system can also detect very low to no movement or situations in a patient, such as when the patient's breathing, heartbeat, and other physical motions have stopped.

In a still further related aspect, a badge, nametag, bracelet, or other wearable device which is recognized by the system of the present invention can be worn or carried by the caregiver. The caregiver is associated with one or more wearable devices, which each comprises an identifier (such as a name, number, code, etc.). The wearable device wirelessly transmits to base stations that are in known locations. In another aspect, the caregiver can communicate with the PAC by physical interaction, such as by tapping on the PAC to indicate a completed turn or other event.

These and other aspects of the invention can be better appreciated from the following Figures.

DETAILED DESCRIPTION OF THE INVENTION

Location Sensing—Orientation—Based Location Analysis

Figure 1A:
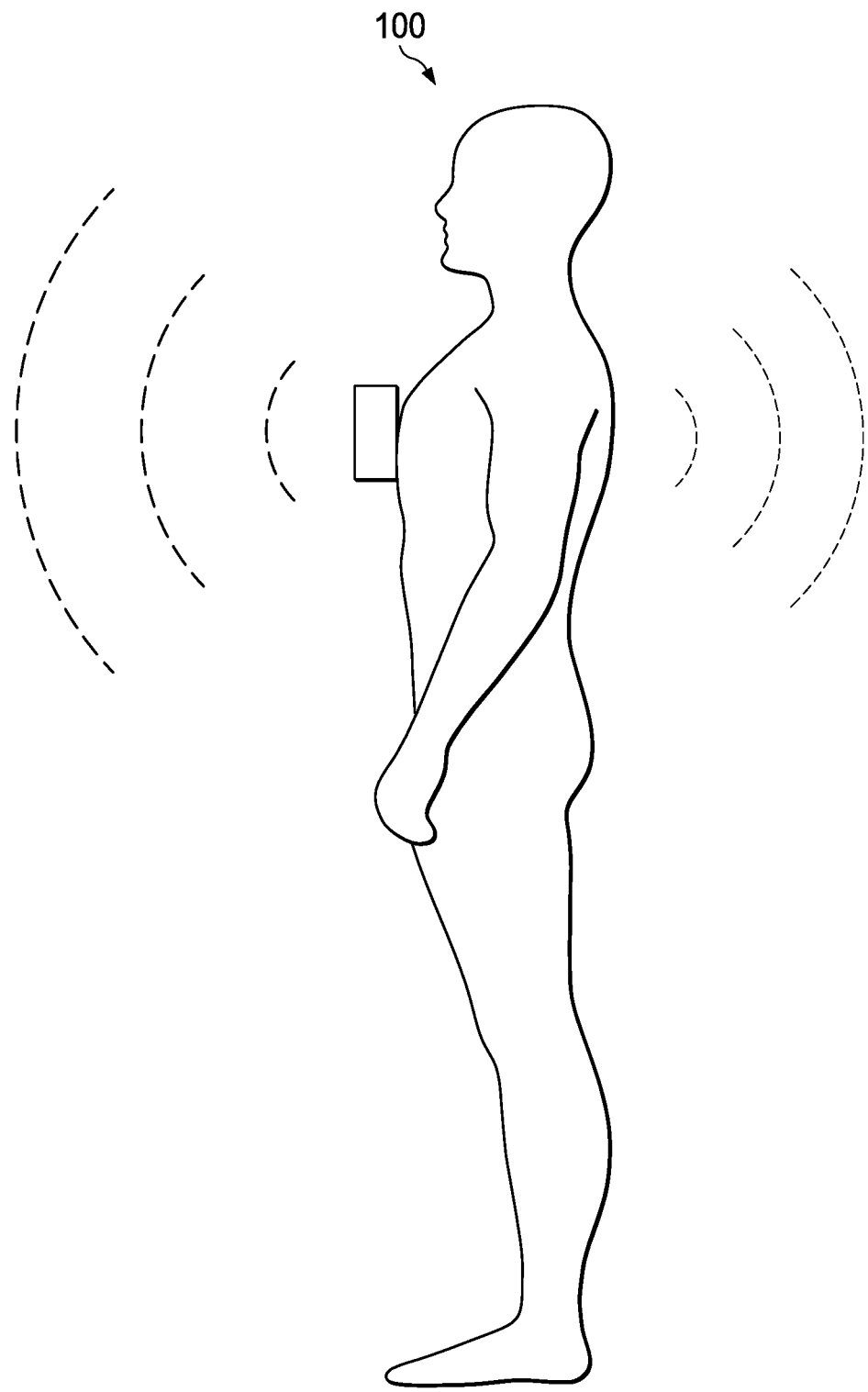
FIG. 1A illustrates a substantially directional transmission profile of an example PAC applied to a patient's chest, according to an example embodiment.

In an aspect of the present invention a more accurate means for determining the location of patients with respect to a care environment is provided. A wireless communicator is associated with a patient, referred to herein as a patient-associated communicator (PAC). The PAC comprises an antenna that is capable of sending or receiving wireless signals. The PAC also has a means for determining its orientation (including the orientation of the PAC's antenna) relative to a patient and/or the environment. Such means for determining the PAC's orientation include an accelerometer, gyroscope, or magnetometer. In some implementations, the PAC has a directional antenna. The PAC can be physically attached to a patient, or can be in close proximity to a patient, or can be in a known location/position/orientation relative to a patient. The PAC can communicate with other PACs and can also communicate with external wireless communicators that are located at fixed/known reference locations within the patient care environment. Communicators that are located at fixed/known reference locations within a patient care environment will be referred to herein as environmental reference communicators (ERCs).

There are various ways that the location of a PAC (and hence the location of the corresponding patient) can be determined. A PAC can communicate with one or more ERCs, and since the location of ERCs is known, the location of PACs can therefore be determined by analyzing the relationship of a PAC to the various ERCs. Since the approximate transmitting range of PACs and ERCs is known, an approximate location for a PAC can be determined simply by knowing which ERCs a PAC is communicating with. If a PAC is communicating with an ERC, then the PAC (and therefore the corresponding patient) must reside within the same general location as the ERC (defined by the transmitting range of the PAC/ERC).

Patient location can be determined more accurately by analyzing time of flight, perceived signal strength, or via triangulation of a PAC relative to multiple ERCs. These methods are well known to those familiar in the art.

Disclosed herein is a novel method and device for improved patient location tracking. In one implementation of the present invention, the patient-associated communicator is physically attached to a patient, such as on the patient's anterior chest. Given that the human body attenuates wireless signals, a wireless communicator that is placed on the patient's anterior chest may transmit more effectively in an anterior direction, and less effectively in a posterior direction (since the signal may be attenuated by the body tissue). As a result, the antenna of the patient-associated communicator can be configured to be directional. Since the human body can have a variety of different shapes, sizes, tissue densities, etc. the amount of signal attenuation can vary from person to person. To further accentuate the directionality of the antenna and provide a more consistent transmission profile across subjects, in some embodiments a radio-opaque backing can be applied to one or more sides of the communicator, such that wireless transmission occurs preferentially in one direction.

As the patient-associated communicator changes location/orientation within a care environment, it will become more or less visible to different environmental reference communicators. Given that the PAC has directionality, when the PAC rotates along a single axis in a fixed location, it will become more or less visible to different ERCs. For example, consider a patient care environment that has a single PAC and a single ERC. When the PAC is oriented directly towards the ERC, the ERC can detect the presence of the PAC. Using the perceived signal strength, or time of flight, the location of the patient can be more accurately determined. However, as the patient begins to rotate along an axis but remains in a fixed location (i.e. the PAC changes its orientation relative to the ERC), the perceived signal strength and/or time of flight will change. This example illustrates how changes in not only the location, but also the orientation of a directional PAC relative to an ERC will change the perceived signal strength. Therefore, the location of a directional PAC can be more accurately determined if the orientation of the PAC is known.

FIG. 1A illustrates how a PAC applied to the anterior chest can have a substantially directional transmission profile. The transmitted signal is attenuated by body tissues, radiopaque coatings, or other means, and hence signal strength varies with direction relative to a receiver.

Figure 1B:
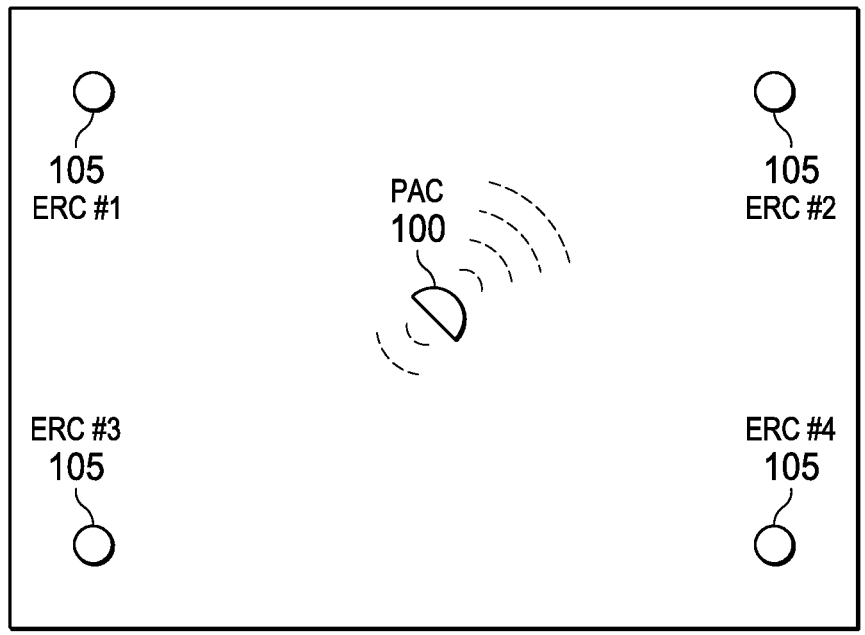
FIG. 1B shows the perceived signal strength at each of a plurality of ERCs near the directional PAC of FIG. 1, illustrating that the perceived signal strength may vary based on the orientation of the PAC relative to each ERC, according to an example embodiment.
Figure 1B:
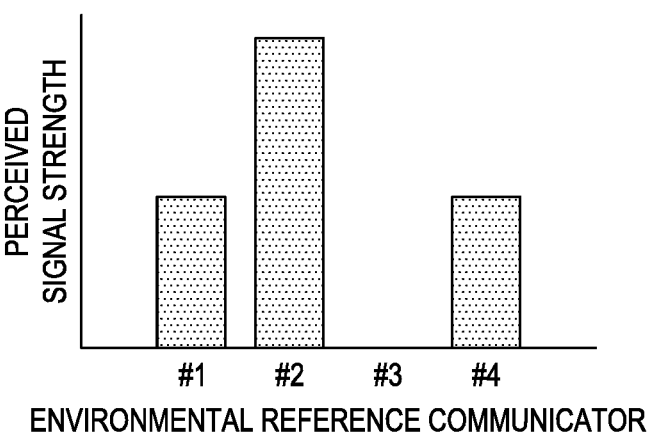

In the example of FIG. 1B, although the directional PAC is equidistant from each ERC, the perceived signal strength varies based on the orientation of the PAC relative to each ERC. In the example above, the perceived signal strength between ERCs #1 and 4 and the PAC is relatively low, and thus the calculated distance between ERCs 1 and 4 and the PAC may be determined to be large. There is no signal transmission between ERC #3 and the PAC. However, the perceived signal strength between ERC #2 and the PAC is high, and thus the calculated distance may be determined to be small. Although the actual distances between each ERC and the PAC is the same, the calculated distances vary based on the orientation of the PAC relative to each ERC.

Figure 1C:
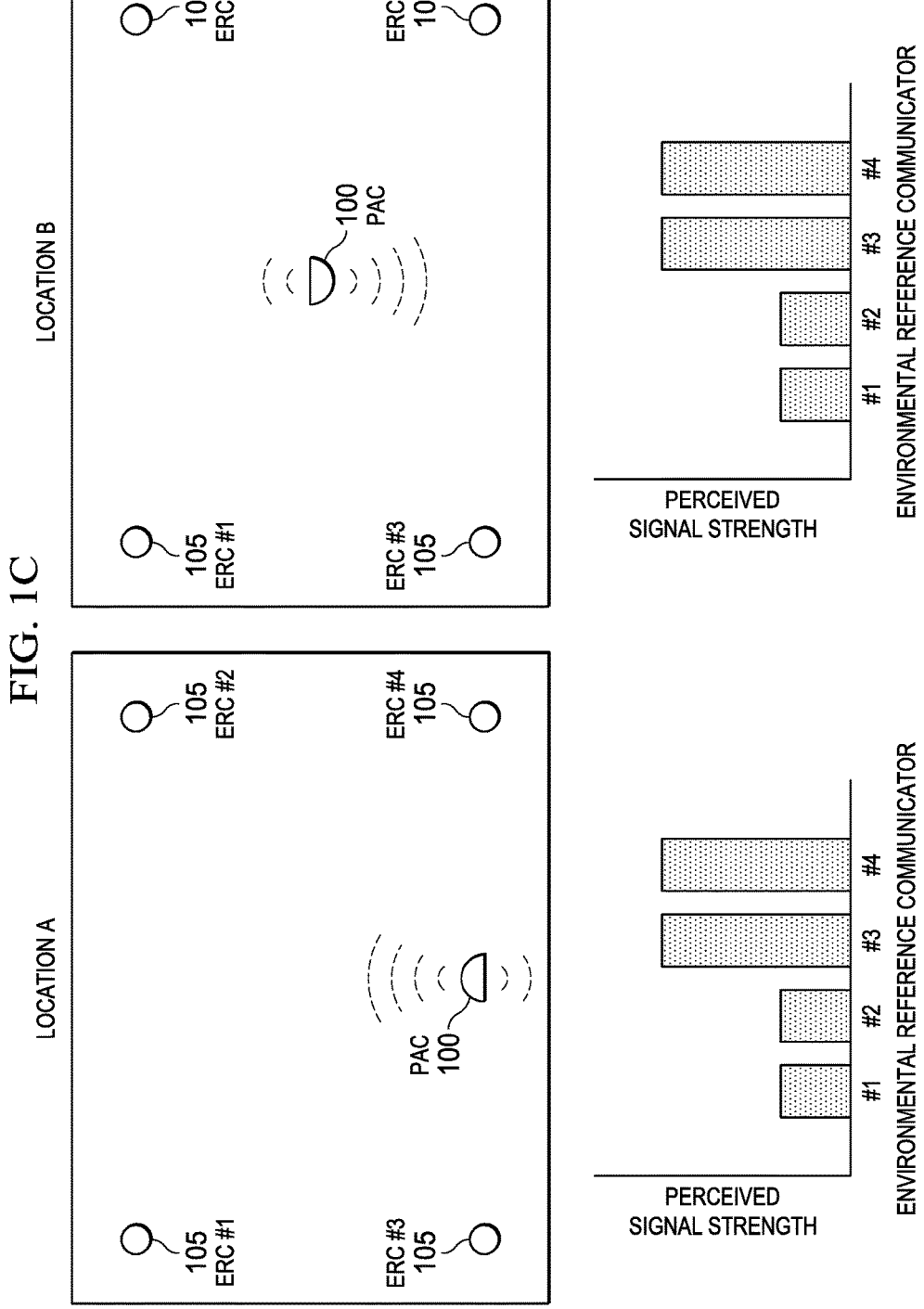
FIG. 1C shows a similar perceived signal strength profile between the example PAC and the four ERCs resulting from two different position-orientation combinations of the PAC, according to an example embodiment.

In FIG. 1C, the perceived signal strength profiles between the PAC and the four ERCs is the same, although the PAC is in different locations (Location A vs. Location B). The signal strength profiles are the same, despite the different locations, because the orientation of the PAC relative to the ERCs has changed. This example illustrates how the location of a directional PAC cannot be accurately determined based on perceived signal strength alone.

In an aspect of an embodiment of the invention, a novel method for improving the accuracy of location tracking of a directional PAC by providing information regarding the orientation of the directional PAC relative to ERCs. As mentioned previously, the PAC has a means for determining the orientation of its antenna relative to the patient and/or the environment. The orientation of the PAC's antenna can be determined using sensors such an accelerometer, gyroscopic sensor, and/or magnetometer. The PAC will communicate its spatial orientation relative to an ERC. With knowledge of the orientation of the PAC relative to the patient, the perceived signal strength can be more accurately analyzed to help determine the location of a PAC relative to ERCs.

In order to know how the orientation of a given PAC affects the communication to an ERC in terms of perceived signal strength, time of flight, etc., a system calibration step can be performed. When the system is initially installed and the environmental reference communicators are placed in relatively known locations, a calibration step can be completed to determine the communication readings (signal strength, time of flight, etc) from a PAC at a given location for all possible PAC orientations, or a subset of common orientations. This calibration step can be done with a calibrating unit that simulates the patient (at least in terms of RF or wireless transmission) and rotates through various different orientations.

This calibration can be done for bed locations such that bed assignments to patients are automatically made. The calibration can also be done for other location of chairs, rooms, lounges, bathrooms to help determine location of a patient. If more than one location is possible after the location analysis, the user may be given a set of possible locations to choose from. This helps by narrowing down the choices to allow for simpler interaction with the system. The data of user entries and patient orientation analysis can be used for the system to learn over time to improve its location analysis. It can also be used for detecting, alert, or learning from new obstructions, such as furniture, etc over time. The same orientation based location analysis can be used with time of flight or other location analysis as well. The same orientation based location analysis can be used for objects such as equipment as well.

It should be noted that the location of any object (including patients) can be determined more accurately using the method and device described herein. For example, equipment can be tagged with a communicator. The equipment will attenuate the signal in certain directions. Therefore, if the orientation of the communicator is known, the system can factor this information into the location mapping system to more accurately determine the location of the equipment.

Since PACs can communicate with each other, if the location of one PAC is determined, then, for at least some embodiments, the system can allow PACs to functionally serve as an ERC for other PACs. In this way less ERCs may be used or the location determination may be more robust or accurate with more effective ERCs.

Once an initial calibration step is done, a user is presented with location information of the PAC. The system may have analyzed the location of the PAC incorrectly. A user can then enter the correct information. This corrected information can be used as data to help further train the system. Additional calibration steps can also be used. In an alternative approach, the system can act with no initial calibration, and a user enters the initial location and/or orientation information. The system uses one or more user inputs to train the system on the location and orientation information. If the system detects small changes in the communication signal information (signal strength, etc) between the PAC and ERCs and the location information is still correct, the system can also use that data to train the system as to the range of acceptable signal information for a given location. The system can know the location information is correct, by getting confirming input from the user, by getting no corrections from the user, or by receiving position information that is consistent with expected data, etc.

Location Sensing—Bed Beacon

Another variant is to have a wireless communicator associated with each patient location. For example, a communicator may be placed relative to each patient bed. The sufficiently close proximity between the patient sensor and the bed beacon/communicator will allow for automatic association between a patient and a bed. Proximity sensing can be done with various methods including signal strength or time or flight. The communication strength of the beacon or sensor can be small as well to prevent ambiguity of assignment, where a patient can be associated with more than one bed or a bed can be associated with more than one patient. If there is ambiguity, the assignment can be narrowed down to a few patients or beds to simplify the association process. The bed beacon can be plugged in or battery powered. It can be placed on the bed or the wall, as shown at 100 in FIG. 8B. In some embodiments, the beacon can also display information visually or audibly.

Pressure Ulcer Documentation Using Visual Data Logging

In an aspect of the invention, an embodiment in accordance with the present invention provides an improved method for photographic or videographic documentation of certain patient conditions, including skin lesions such as pressure ulcers.

Figure 1D:
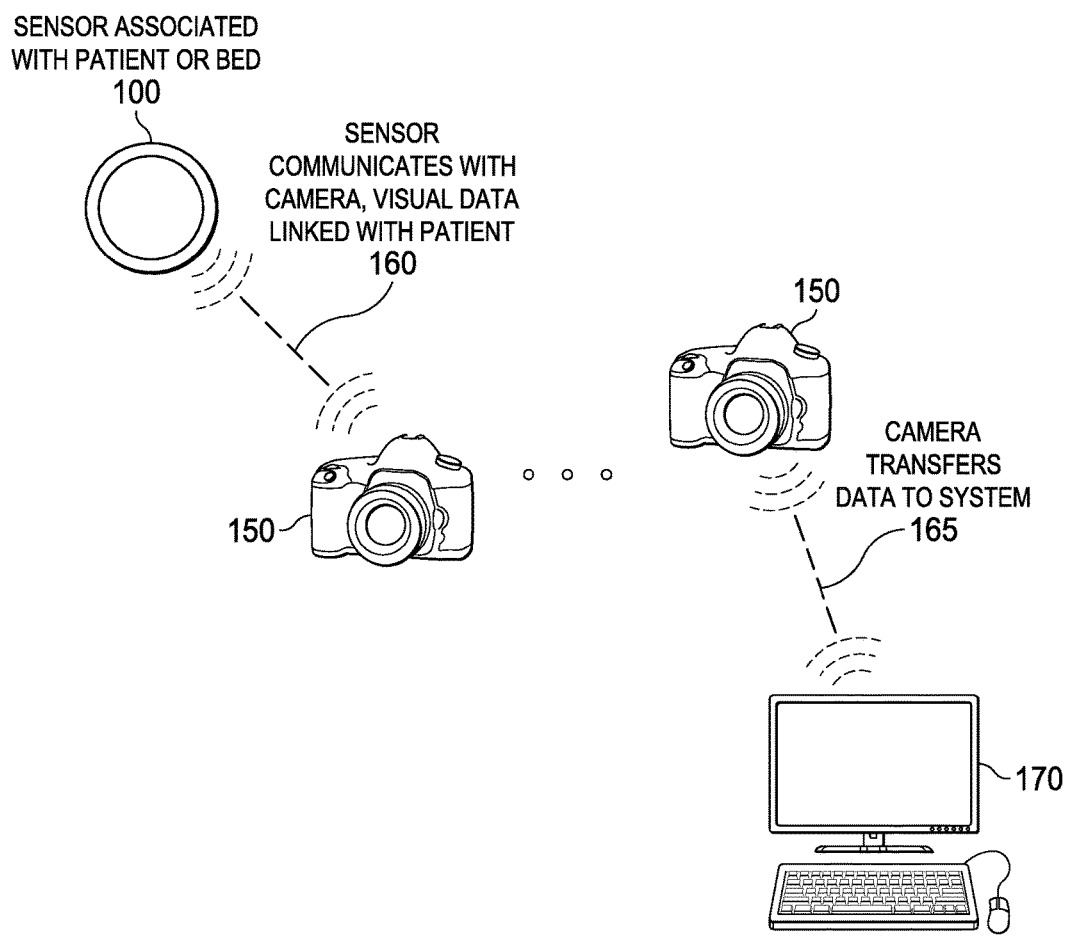
FIG. 1D shows a camera used to visually document the presence of a pressure ulcer and transfer such visual data to a caregivers' data processing system, according to an example embodiment.

In one exemplary instance of this aspect of the invention, shown in FIG. 1D, a camera 150 is used to visually document the presence of a pressure ulcer and this visual data is then automatically logged and associated with a specific patient. In such a fashion, users are provided with an improved method for documenting the presence, absence, current condition of, or progression of one or more pressure ulcers for a particular patient. Visual data is captured at the bedside where it is automatically associated with a specific patient and then stored.

As described in greater detail hereinafter, the camera of the present invention automatically associates the recorded visual data with a specific patient. In one implementation, this association is accomplished, in part, by utilizing a camera 150 (FIG. 1D) that can wirelessly transmit, receive, or transmit and receive data. The camera can utilize any number of wireless communication protocols, such as Wifi, RFID, Zigbee, 802.15.4, infrared communication, Bluetooth, or any other communications protocol known to those skilled in the art or later developed as shown at 160 in FIG. 1D.

As one example, the camera communicates with wireless communication units that are associated with specific patients, referred to hereinafter as patient-associated communicators (PACs), shown as 100 in FIG. 1D. The communicator can be associated with a patient identifier, such as the medical record number (MRN or MR#), electronic medical record (EMR), date of birth, social security number, patient name, demographic information, diagnosis, treatment team, location (including room number, unit number, etc.), or any other patient data or other sufficiently unique identifier. The communicator 100 can be in close proximity to the patient, worn by the patient, attached to the patient, in a location associated with the patient such as a room or bed, or in fixed/known locations relative to the patient. The PACs can be linked to a specific patient with one or more of the following: The camera can communicate with PACs located within transmitting range of the camera, for those implementations where the camera utilizes wireless communications. Data from the PACs (i.e. patient name, MRN, etc.) is communicated either wirelessly or wired as shown at 165 in FIG. 1D, and can be stored in the caregiver's data processing system, shown at 170, along with any visual data subsequently obtained by the camera. If there are multiple PACs within communicating range of the camera, the camera can determine which PACs reside in closest proximity to the camera by analyzing perceived signal strength, time of flight, or other modalities known to those familiar with the art. In such an arrangement, the PACs enable an image to be automatically associated with a patient. This reduces the need for users to enter patient information manually and helps with workflow. The relative or absolute distance between the camera and PACs can also be determined. The communicating range of the camera and/or PACs can be modified such that more or fewer PACs become visible to the camera. In some implementations, the communicating range of the camera and/or PACs can be limited such that only a single PAC becomes visible to the camera. The camera may display a list of all possible PACs within communicating range of the camera or of the PACs that are closest to the camera. By displaying the nearby PACs, which may indicate that there are multiple patients that the system could automatically link an image to, the user can select the proper combination of image and medical record. This avoids mistaken linking while at the same time substantially reducing the need to enter data, again improving workflow. The user may then select the PAC that is to be the focus of visual data collection. Any subsequent visual data collected by the camera (pictures, videos) is then automatically linked with data obtained from the selected PAC (i.e. patient name, MRN, etc.), and the linked data is sent to a central server for logging.

Figure 2:
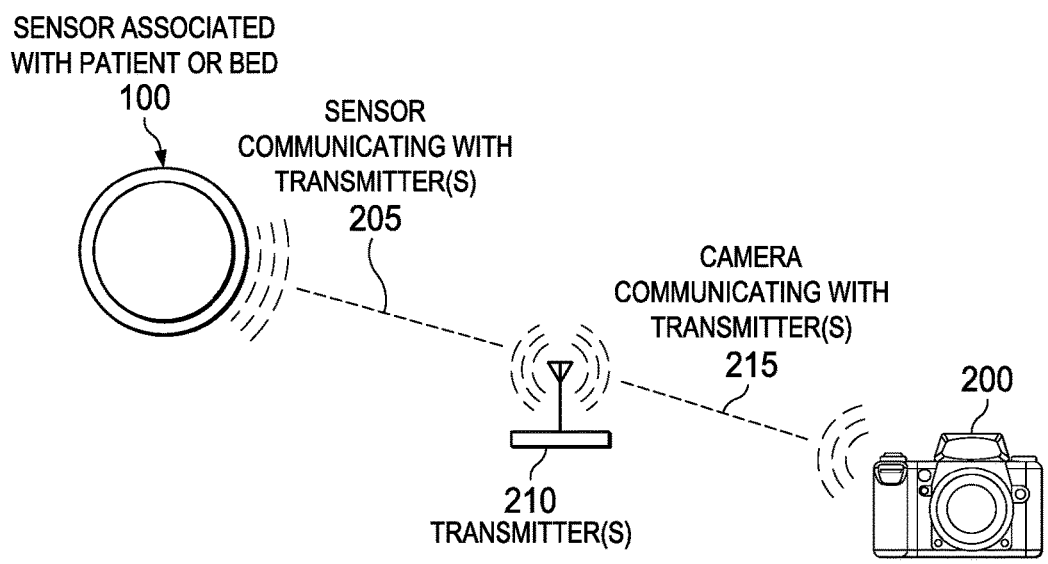
FIG. 2 illustrates a second aspect of the invention, in which a sensor associated with a known reference point cooperates with a camera to link visual data relating to a patient's condition to the patient in the caregiver's data processing system.

Similarly, as shown in FIG. 2, the camera 200 may include a transmitter/transceiver that sends signals 215 to an environmental reference communication device or ERC 210 associated with a patient or the patient's room, to identify with whom any given visual data should be associated. Similar methods as noted above allow for the subject to be identified specifically when more than one ERC can be communicated with. Similarly the camera location, either absolute or relative, can be identified and the determined location of the camera can be associated with the known location of a subject. The location can be identified by proximity to other known entities or locations. Alternatively, the location can be determined via means such as signal strength or time of flight analysis to other transmitters/transceivers, including nodes, patient sensors 100, or GPS. Other sensors can be available on the camera including temperature, humidity, light sensors, audio sensors/microphones, orientation sensors, etc.

In various embodiments of the invention, there are several ways in which a patient's name and/or demographic information can be automatically associated with images taken of the patient in real-time. One way this is accomplished is by having a wireless sensor associated with a specific patient.

The sensor has a unique ID, which is then assigned to a patient. This assignment process can either be manual (i.e. manually assigning sensor ID to patient's MRN # in computer system) or automatic (i.e. barcode reader scans patient sensor and then patient ID bracelet). There are many ways of assigning the patient sensor to a specific patient, which are well known to those familiar with the art. The camera (or multimedia device) has a built-in wireless transceiver that can detect any patient sensors within its general proximity. The sensor ID (and/or the name associated with said sensor) is then automatically displayed on the camera. The user then selects the correct sensor ID (or patient name), and any pictures or images subsequently obtained are associated with the sensor/patient, until a new sensor/patient is selected.

Figure 3:
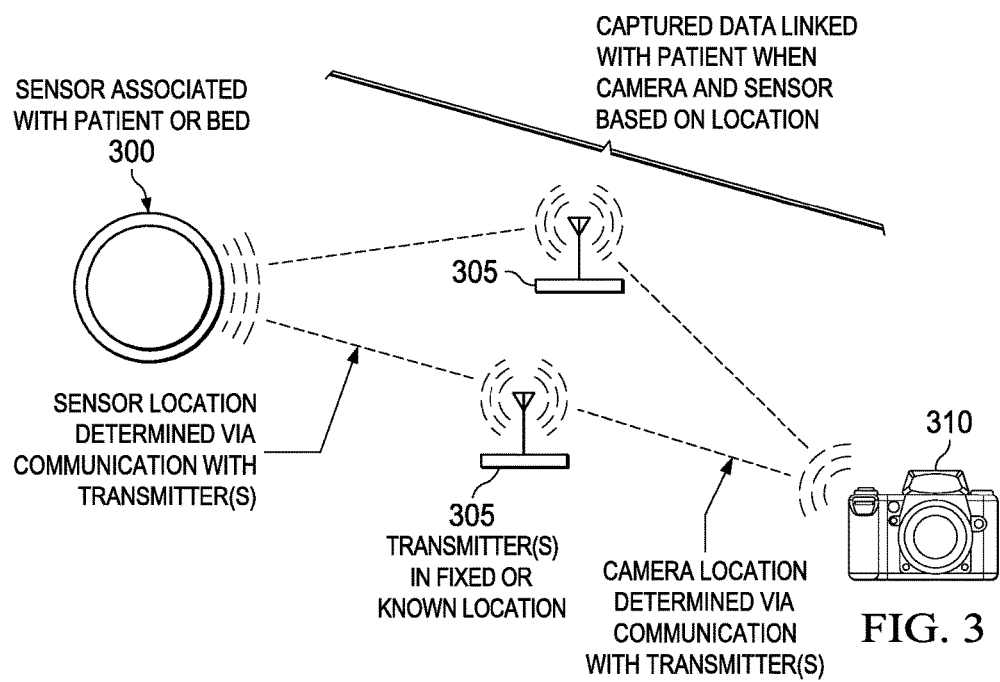
FIG. 3 illustrates a third aspect of the invention, in which multiple transmitters in known locations within a room communicate with a camera and a communicator affixed to the patient.

FIG. 3 illustrates a further aspect of the invention, in which a plurality of transmitters 305 are positioned in fixed or known locations, and one or more sensors 300, each associated with a different patient, move within space observable by the camera 310. The camera location can be determined by triangulation with multiple base stations, and the accuracy of the camera location is improved by knowing the orientation of the transceiver on camera. In such an embodiment, patient location can be determined by triangulation with multiple base stations, again with accuracy improved by knowing the orientation of the transceiver, or communicator, on the associated patient. Because the camera is linked to the patient sensor, the camera and the sensor combination associates the visual data with the correct patent.

The camera can upload the data it captures wirelessly to the system, such as via Bluetooth, Wifi, Zigbee or another established or custom wireless transfer protocol. The wireless transfer can be accomplished to a computer or computing station at the nursing station or other central location or it can be accomplished through an existing wireless network, such as the patient sensor network, Wifi, or communication node network. The data can also be transferred in a wired fashion, such as by USB, firewire, Ethernet, etc.

Alternatively, the data can be transferred by other means such as by USB stick, memory card.

The location of the image taken of skin or a pressure ulcer can be identified by the user. This can be accomplished by a list of locations or parameters to help define location, free text entry, or 2D or 3D image-based selection, where the user can, for instance, point to or drag and drop a location on a visual representation of the patient. A similar 2D or 3D representation can be used to identify areas that are at risk, have existing wounds, or have lines, etc., that be beneficial to avoid or target for repositioning.

Image Standardization

Figure 4:
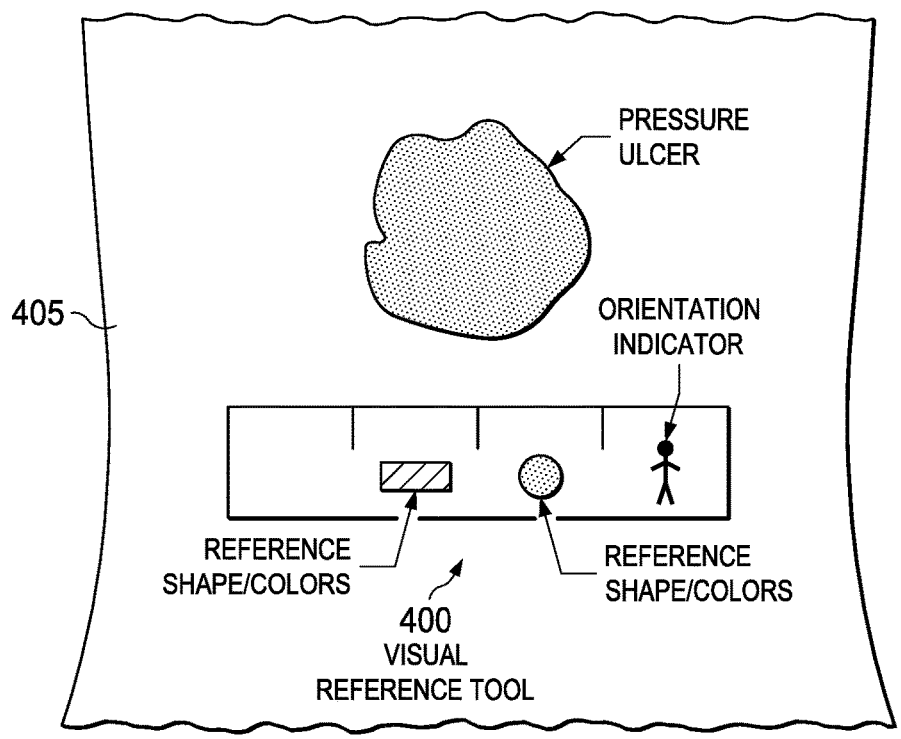
FIG. 4 illustrates a technique for assisting in image standardization and image capture.

In an aspect of the invention, techniques can be provided to permit visual data obtained from a camera to be standardized. Such standardization can, in some implementations, improve documentation. Image characteristics that may need to be standardized include image orientation, viewing angle, viewing distance, brightness, color, etc. To assist in image standardization, a visual reference 400 may be placed within the field of the image 405, as shown in FIG. 4. This visual reference can take the form of a sheet, ruler, or sticker of a known size, shape, and color. The visual reference may include standard reference lengths, colors, and orientation indicators. The camera, or other image processing functionality provided by the system, can then process the image according to the appearance of the reference such that all images conform to the same standard.

Figure 5:
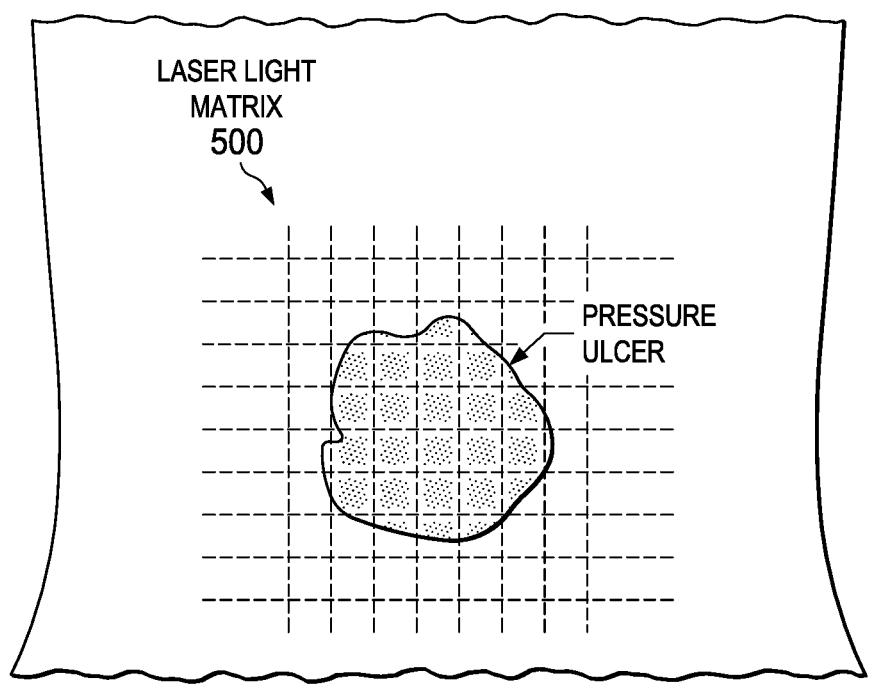
FIG. 5 illustrates an alternative technique for assisting in image standardization and image capture.

The reference may also take the form of a light source, as shown in FIG. 5. For example, one or more lasers 500 can be shone from the camera unit, or from another source, onto the image. The laser light is directed towards the area of interest. The laser light may have a combination of features, including known size, shape, orientation, and spread. Image standardization can help better track the current condition and progression of an area of skin or a wound.

Figure 6:
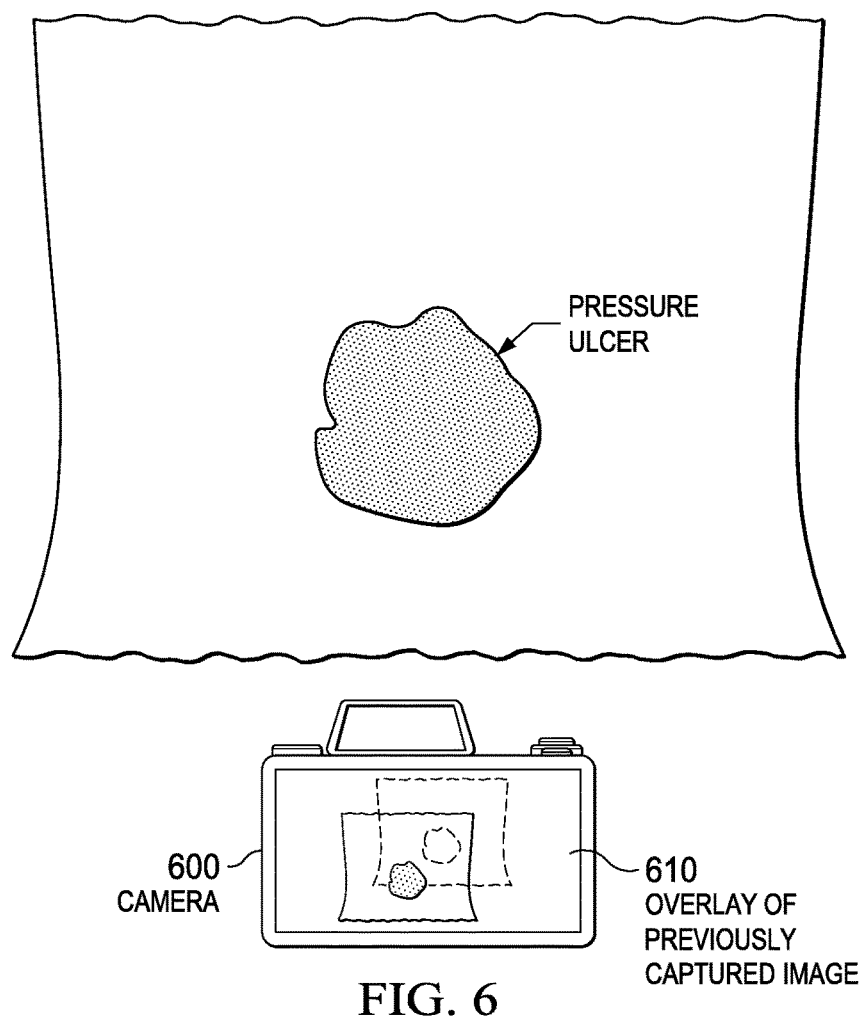
FIG. 6 illustrates a technique for visually comparing the current and prior status of an area of interest.

In FIG. 6, laser light is focused on an area of interest (i.e. a pressure ulcer). In an embodiment, the laser light has a matrix orientation as shown in FIG. 5, which is viewable by an associated camera 600. As the viewing distance increases, the area within individual squares of the matrix increases. The laser light also has one or more known wavelengths, such that the color can be standardized. The laser light may, but need not, have a wavelength in the visible spectrum as long as that wavelength can be viewed by the associated camera or other imaging device.

To aid in documentation, images can be timestamped in at least some embodiments. Timestamping images will allow for the creation of a temporal record of how a wound or area of interest evolved over time for a specific patient.

In some situations, it may be necessary to take a temporal series of pictures of a patient, or of a patient's condition. For example, pictures of a patient's pressure ulcer may be taken daily in order to track progression of the ulcer. In order to allow for more consistent data gathering, an overlay 610 of a prior image can be projected onto the camera, also as shown in FIG. 6. The user can use this image overlay to help re-approximate viewing angle, distance, orientation, etc.

Indicators on Sensor

Figure 7A:
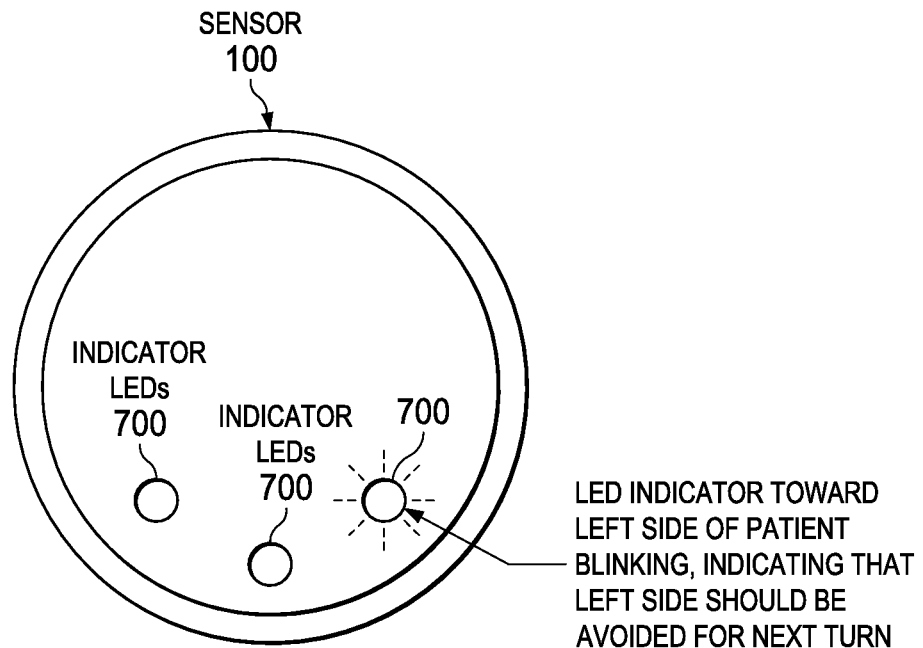
FIGS. 7A-7B illustrate an embodiment in which indicators such as LEDs are provided on the sensor so as to be visible through the housing of the sensor, for assisting in indicating patient position.
Figure 7B:
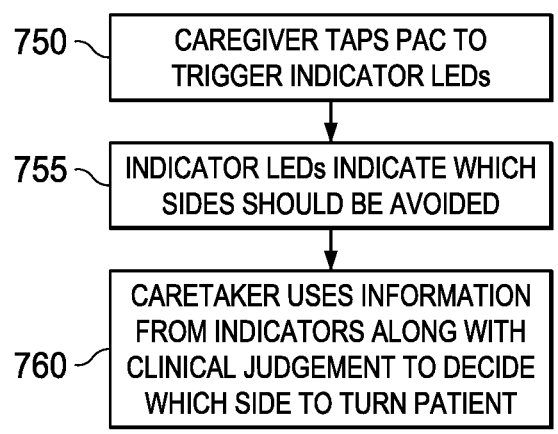

As shown in FIGS. 7A-7B, in some embodiments there may exist indicators 700 on the sensor, for example LEDs, which give information about the patient. These indicators may indicate which side the patient is on, when a patient requires a turn, which area of the body has been exposed to the most pressure, which direction a patient should be turned onto, or when a patient has been turned sufficiently to satisfy a turning protocol or to depressurize a given area. For example an LED on the left side may turn on when the patient is on their left side. Similarly, in another implementation or setting, the LED may be used to indicate when a patient should be turned and in which direction a patient should be turned. The LEDs may also indicate the relative pressurization levels at different body regions.

In some embodiments of these sensor indicators, the indicator may be displayed only when triggered. Triggering, as opposed to being on constantly or periodically, can allow for reduced battery consumption and reduced light pollution. In some embodiments, the caregiver may provide the trigger as shown at 750. The trigger may take the form of one or more of a single tap or sequence of taps on the sensor as discussed hereinafter in connection with FIG. 9, exposure of the sensor to given threshold of light, a switch or button on the sensor, or a wireless communication (which may include RF, sound, light) to the sensor, in response to which the indicator LEDs indicate, for example, which sides should be avoided as shown at 755, allowing the caregiver to make clinical judgments at 760. In one implementation of the light threshold trigger, the threshold of light would be exceeded when the caregiver lifts the sheets or clothing to view the sensor, and the LEDs would then come on. The wireless communication can be provided by the caregiver, either by sound or wireless communication generation. In one implementation of the wireless communication, the caregiver can carry an RF transmitter that transmits a signal to the sensor when the caregiver is near or when the caregiver presses a button on his/her transmitter. The transmitted signal causes the indicators on the sensor to display.

Patient Self Roll

Figure 8A:
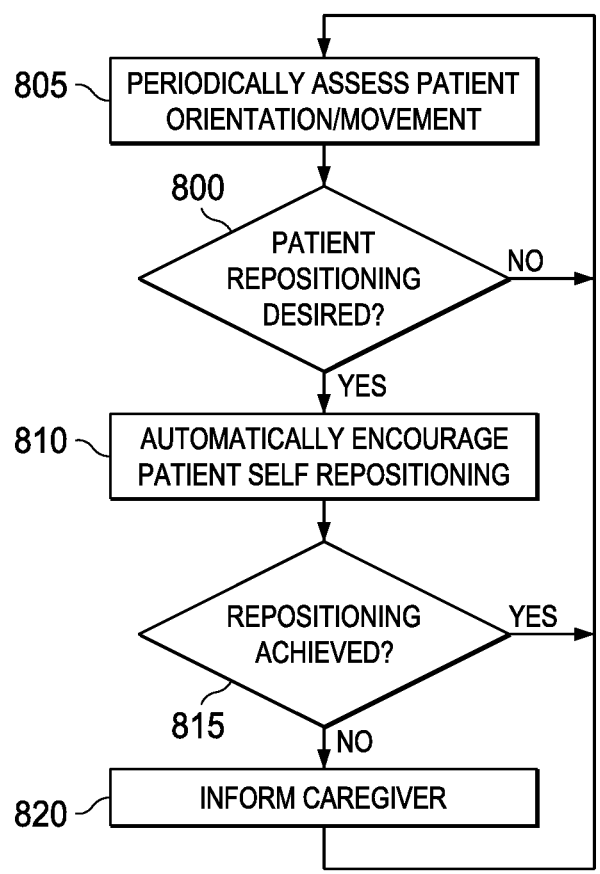
FIGS. 8A-8B illustrate an embodiment of the invention in which the patient is encouraged to self-roll.
Figure 8B:
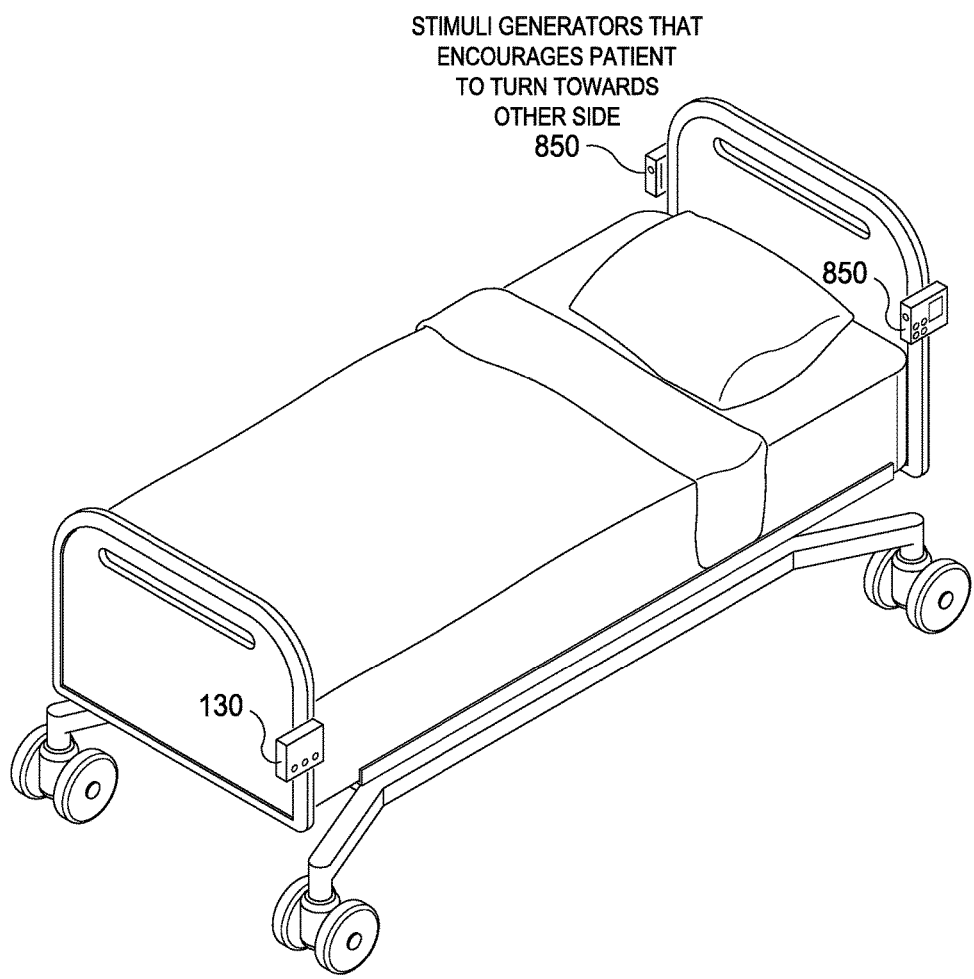

Patients can often reposition themselves to some degree. As shown in FIGS. 8A-8B, in an aspect of the invention the system may be used to encourage repositioning and/or to encourage a somewhat specific direction of repositioning, as shown at 800. For instance, if it is desired to have the patient reposition onto their left side, 805, encouragement may be given for the patient to roll onto the left side as shown at 810. Such encouragement can include:

Audio guidance, which may include voice guidance, the voice of a known person (patient himself/herself, loved one, caregiver, famous person, song, music), or a generated voice Visual guidance, lights, lights of increasing brightness, lights of varying color or brightness, blinking lights Noises, Beepers, Sirens Physical guidance, including a push, nudge, elevation or angle change of the support surface, a pressure change of the support surface, vibration, tickle, such as via a feather, etc.

Temperature

One or more of these methods can be used in combination either simultaneously or in spatial or temporal relation to one another. Certain stimuli may encourage the patient to turn away or towards without waking up or greatly disturbing sleep. The light or audio or physical stimuli are examples. Patients may naturally turn away from sound, lights, or nudges. In this way a patient may be encouraged to reposition according to a protocol or avoid pressure on certain areas. A patient self-turn reduces the need for caregiver interaction and promotes patient independence. If a patient does not reposition sufficiently, determined at 815, a caregiver can be notified as shown at 820. In an embodiment, the stimuli for turning can be external to the patient sensors, such as a unit on the bed, as shown at 850 in FIG. 8B.

Caregiver Units

In an aspect of the invention, the caregiver can also carry components of the system with them. In one implementation, the caregiver has a badge, nametag, bracelet, or other wearable device which is recognized by the system of the present invention. The caregiver is associated with one or more wearable devices, which each comprises an identifier (such as a name, number, code, etc.). The wearable device wirelessly transmits to base stations that are in known locations. As can be appreciated from FIG. 9, discussed hereinafter, using the methods previously described in the section on "Location Sensing", the system can determine when the caregiver is in a given room, provide information about when the caregiver is interacting with a patient or other caregiver, or can determine when the caregiver is in any particular location, such as a room, the nursing station, supply closet, or hand-washing area. The location of the caregiver or indication of caregiver-patient interaction can be used to determine when a caregiver helps to reposition a patient. This can be used to determine who is repositioning a patient and to determine if sufficient self turns by the patient are being performed. Caregiver devices can also be used to login to the system when entering information or to help pull up or assign patient information or data related to the patient(s) that the caregiver is assigned to. Devices can be wirelessly charged, passive RFID based, or charged by a physical connection. In one implementation, the devices can be charged inductively by having the device placed in close proximity to a charging unit, such as a charging surface or box. The wearable device can also display or present information visually or audibly. The unit may also indicate when alarms/notices are given. For instance a nurse may be given an audible message or a written message to indicate that a given patient requires turning, or has exited bed, or has fallen. Lights, such as LEDs, may give information, including alarms as well.

The caregiver can also carry a device, such as a handheld reader or scanner. This reader can be used to scan or wirelessly communicate with one or more of patient sensors, a bed or room sensor, a patient ID tag/bracelet, etc. In an embodiment, the device can communicate with a computer or with a sensor or node network or other wireless communication network. In some embodiments, the device can include a barcode reader. In various embodiments, the device can be handheld, attached to a computer, a phone, or a bracelet. The device can also have an audible or visual information display as described above for the wearable device. These devices and the wearable devices can also be used for communication between patients and caregivers or between caregiver themselves, again as illustrated in FIG. 9, discussed below.

Alternating Pressure Mattress Detection

Acceleration and orientation monitoring of the patient may be used to monitor for motion caused by an alternating pressure mattress. The monitoring system of the present invention, by detecting patient accelerations, can determine if a patient is being repositioned sufficiently. Threshold acceleration values can be set, such that if the acceleration threshold is not met in a specified period of time, then it can be assumed that the patient is not being repositioned sufficiently. Alternating pressure mattresses utilize a series of inflatable air cells that inflate in a regular pattern, so as to encourage tissue depressurization of the subject lying on said alternating pressure mattress. This pattern of inflating/deflating air cells will generally cause rhythmic accelerations in a patient lying on the support surface. If no rhythmic accelerations are detected that are consistent with the known pattern of the support surface, then it can be assumed that the alternating pressure mattress is not turned on or is not functioning properly. Specialty support surface actions, which include alternating pressure or repositioning, may cause characteristic accelerations on the body of the patient. For instance, many support surfaces that provide alternating pressure or repositioning do so by inflating or deflating air cells within the support surface. This inflation and deflation is often associated with small vibrations form one or more components of the support surface system, such as a pump or compressor.

Figure 9:
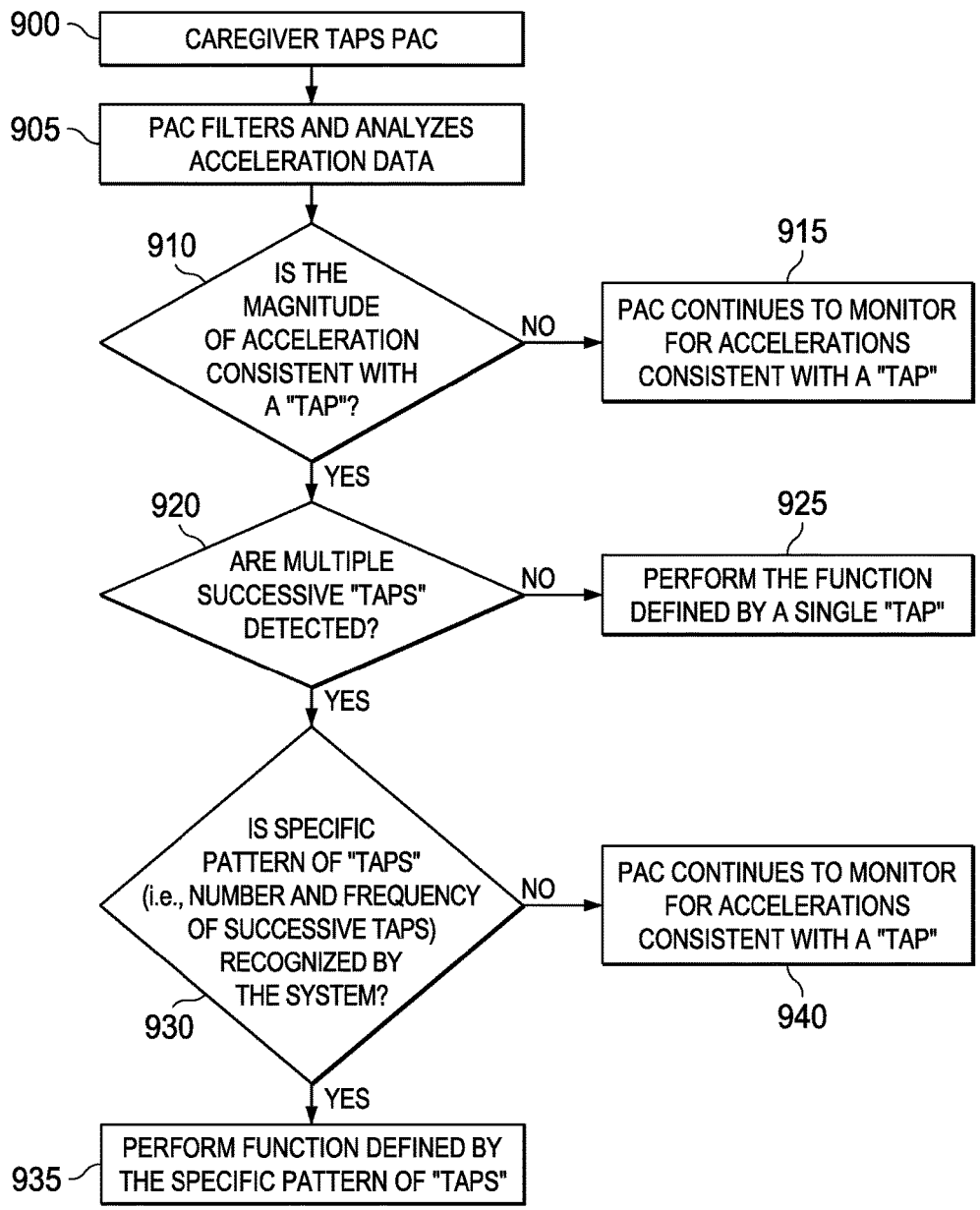
FIG. 9 illustrates an embodiment in which identification of the caregiver is implemented.

In some embodiments, the caregiver can communicate with the monitoring system of the present invention by physically interacting with the patient associated communicator, such as, for example, by tapping as shown at 900 in FIG. 9. In such embodiments, the accelerometer and software on the sensor can be configured to monitor for taps to the PAC, shown at 905-940. In such a manner, a caregiver can tap the PAC to communicate with the system. This communication method can be used to communicate that a caregiver provided a repositioning procedure or that the caregiver is interacting with the patient. A caregiver may also use taps to indicate his or her presence so that the patient sensor can communicate with her via a display, such as one or more LEDs, beeps, or a display screen. The tapping motion causes accelerations/decelerations that can be detected by the PACs onboard accelerometer. The system can be configured to recognize specific patterns of accelerations/decelerations in order to communicate information with the system. The magnitude of acceleration/decelerations that are considered to be consistent with a "tap" can be predefined in the system. Furthermore, different patterns of successive taps can be used to communicate different information, as at 935. As such, the PACs accelerometer functions as an input device for caregivers. For example, if a caregiver wants to inform the system that they are physically present with the patient, they may tap the PAC in a specified pattern, such as two taps at ~1 Hz. As another example, if the caregiver wants to activate the PACs onboard LEDs (which can visually display data such as cumulative pressurization time on each side of the body), they can tap the PAC three times at ~1 Hz. Those skilled in the art will recognize that there are various methods of communicating with the monitoring system via the PACs onboard accelerometer and associated processing algorithms.

Sleep Monitoring

The system can monitor for characteristic movements associated with different indicators of sleep quality. These characteristics include apnea and movement, activity, or orientation during sleep. Reports can then be given about sleep quality to patients and caregivers.

Feedback to Support Surface

In some embodiments, the system can include a pressure measurement system which can produce a pressure map of reasonable precision that then feeds back to a support surface. This pressure sensor system, feedback, and support surface can be a standalone system or it can interact with a sensor network. Knowing where pressure is higher than desired allows for a support surface to automatically respond by optimizing the pressure experienced by a patient. If the support surface is unable, by its automatic response means, to correct for the undesired pressure, it can alert a caregiver to decide about providing further care. The data can be used to inform treatment and parameters for care.

Monitoring Mobility/activity to Determine need for DVT Prophylaxis

Figure 10:
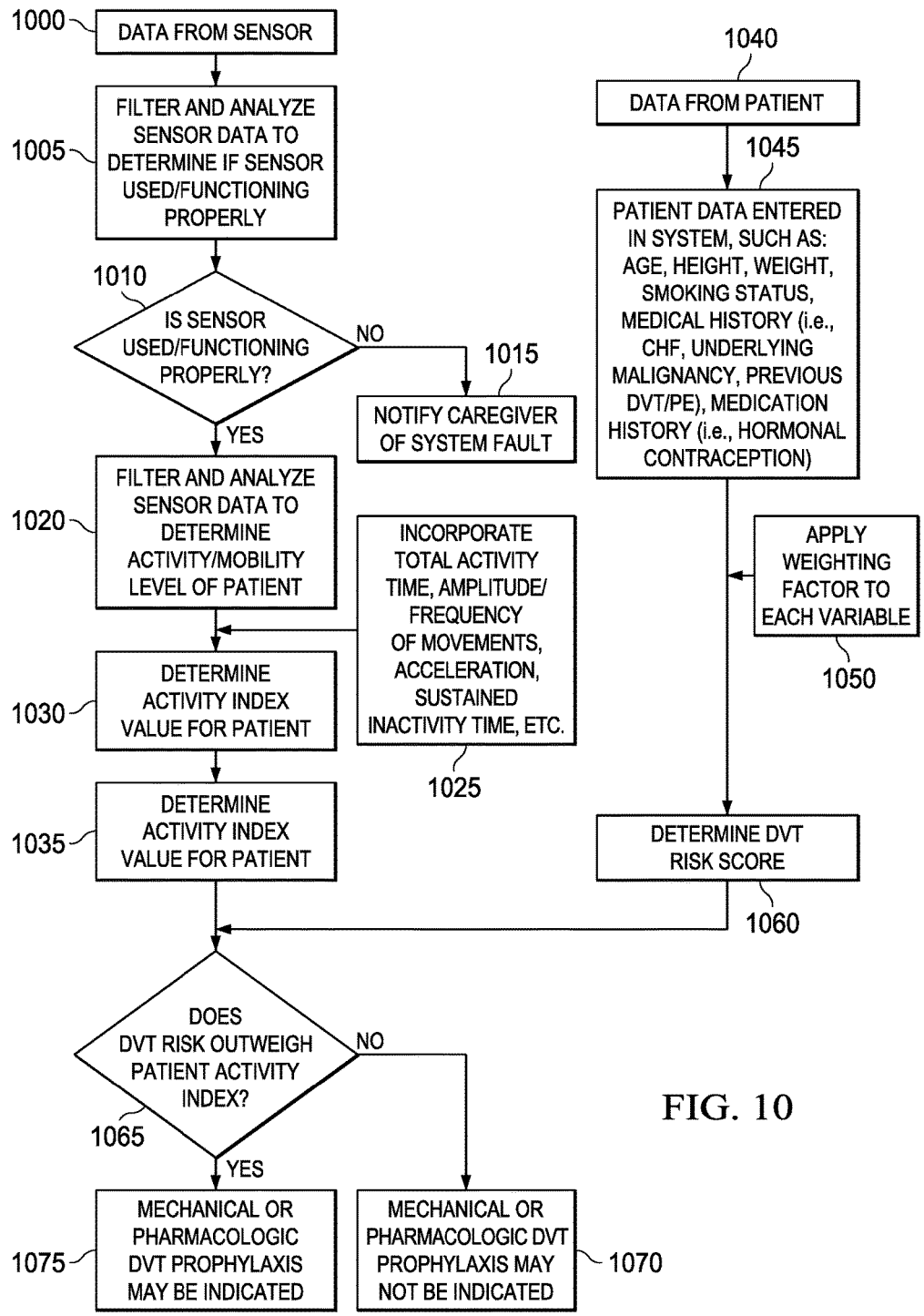
FIG. 10 illustrates an embodiment of the invention in which deep vein thrombosis risk can be monitored.

Patients who are immobilized for long periods of time often require prophylaxis to prevent against deep venous thrombosis (DVT). A DVT is a blood clot that forms in a vein (typically in the leg veins) and often is a consequence of venous stasis, which can occur from prolonged immobility. Patients considered at risk for DVTs will generally receive DVT prophylaxis, which can be pharmacologic or mechanical in nature. Pharmacologic DVT prophylaxis consists of systemic anticoagulation (i.e. heparin, enoxaparin) which is delivered to patients via subcutaneous injections. Mechanical DVT prophylaxis consists of sequential compression devices (SCDs) which are pneumatic compression stockings that are affixed to the legs of patients and then inflate/deflate in order to promote blood flow and thereby prevent venous stasis. As mentioned previously, a major risk factor for DVTs is prolonged immobility. In an aspect of the invention illustrated in FIG. 10, the monitoring system of the present invention is designed to monitor a patient's movements and activity level, and the system can use this information to generate an 'activity index' value for a given patient, shown at steps 1000-1075. The activity index value, shown at 1035, incorporates factors such as: total activity time, amplitude/frequency of movements, acceleration, sustained inactivity time (i.e. how long are the intervals between activity), etc.

Based on the "activity index" score for a particular patient, physicians can decide whether or not DVT prophylaxis is indicated for a particular patient.

To improve the tool, the following factors are incorporated into the analysis, and can be used to generate a DVT "risk score", shown at 1060:

1. Age, height weight, of patient
2. Is patient a smoker?
3. Does patient have CHF?
4. Is patient on hormonal contraception?
5. Malignancy present?
6. Previous DVT or PE?

Note that weighting for all of the variables can be customized by individual physicians, care providers or institutions, such that they can increase/decrease the threshold for DVT prophylaxis. A set of default values can be initially provided. The system is designed to help physicians objectively decide what treatment is best for their patients. Currently, physicians have limited objective information to understand how well a patient is ambulating.

Wireless Communication

In certain cases, wireless communication via a device with an antenna can be affected by the surface upon which the antenna lies. For instance, a device on the surface of the skin can have its antenna performance affected by the electromagnetic and dielectric properties of the body. To shield the device from such effects caused by the body, in some embodiments the device may have material between the body and the antenna that shields or reduces the relative effect of the body on the antenna performance. For instance, a material with a high dielectric constant can be placed on the device between the antenna and the body to serve this purpose.

Automatic Decompression Threshold Calculation

In an embodiment, the system can automatically calculate at least one suggested decompression threshold/interval. The decompression threshold/interval refers to the minimum amount of time that an area of the body needs to experience reduced pressure or no pressure in order to adequately re-profuse that area of the body, thereby preventing ischemia and tissue damage. Once an area of the body has surpassed the suggested decompression threshold/interval, that area of the body can once again be pressurized with lower risk for causing tissue damage. The decompression threshold/interval can be calculated by taking into account factors selected from a group comprising: patient characteristics (i.e. Braden score, age, co-morbidities, size/weight/BMI/body mass distribution, etc.), patient variables (mobility, activity, moisture, nutrition level, experienced or estimated sheer force, medical conditions, vital signs, health conditions, health status, previous skin conditions, and medications, etc.), environmental factors (type of bed surface, ambient temperature, humidity, etc.). One or more calculation schemes can be used by the system and selected by the user.

The system can also allow for a decompression threshold that is variable for any given patient. One common usage is to have a decompression threshold for an area of the body vary with the amount of time the area of the body has experienced pressure. For instance, the decompression threshold can take the form of:

$$D0+D1*[\text{Duration of Pressure}]$$

where D0 and D1 are constants that can be set or varied or vary automatically based on data about the patient or facility.

The system, methods, and devices of the present invention provide an improved method for both calculating the appropriate decompression threshold/interval for a region of the body and also monitoring said region to determine when adequate decompression time has been achieved.

Variables that may affect calculated decompression threshold, include vitals (such as pulse ox, heart rate, breathing rate, blood pressure), time on a given side, duration of pressure orientation, existence of other wounds, patient characteristics (i.e. Braden score, age, co-morbidities, size/weight/BMI/body mass distribution, etc.), patient variables (mobility, activity, moisture, nutrition level, experienced or estimated sheer force, medical conditions, health conditions, health status, previous skin conditions, and medications, etc.), and environmental factors (type of bed surface, ambient temperature, humidity, treatment and prevention techniques used etc.). The system can also accommodate for the ability of different parts of the body may depressurize differently and at different rates.

Indicia on Part Associated with Sensor

An indicia may be associated with a patient sensor so that a user can easily orient the sensor with respect to the patient. The indicia may be a visual indicator, physical feature or shape, or asymmetry. This indicia may be location on the sensor itself, typically the housing or enclosure of the sensor. It can also be located not on the sensor itself, but on something that is in a specific orientation relative to the sensor at some time. One example is a label, stick, adhesive, or element of packaging that can have one or more indicia. These elements may then be separated from the sensor with the user still knowing the orientation of the sensor. Another method is to have a device that can determine the orientation of the sensor, either by mechanical, RF, magnetic, visual, or other communication means.

Flatline Detector

The system can also detect very low to no movement or situations in a patient. Such a situation occurs when the patient's breathing, heartbeat, and other physical motions have stopped. In such a case, the system can very quickly detect such an condition in the patient such that it can note the status and send an alert quickly. In certain cases it would be able to detect the situation in less than a few seconds or in less than one second and alert those who can provide help, possibly within enough time to help the patient. Detection can be much quicker than for systems that detect patient motions suggestive of an abnormal state such as arrhythmias and decompensation. In certain cases there may be ambient movement detected by the system that are not caused by the patient. These movements may easily be disregarded if they fall below the threshold for movements caused by heartbeat or breathing. Alternatively the system may learn what movements are characteristic that don't arise from the patient. Alternatively the system may utilize a separate sensor not on the patient to determine what movements are not arising from the patient and subtract those. Alternatively, the system may use sensors on more than one patient or more than one sensor on a the same patient to subtract out the movements that are common, which may be subtracted as those movements arising from outside of the patient. Electrical signal detection from the patient can be used similarly and where movement is described above, electrical signals are replaced in another implementation of the system. Electrical signals and movement detection can be combined as well to further increase the accuracy and robustness of the detection.

Having fully described a preferred embodiment of the invention, and numerous aspects thereof, as well as various alternatives, those skilled in the art will recognize, given the teachings herein, that numerous alternatives and equivalents exist which do not depart from the invention. It is therefore intended that the invention not be limited by the foregoing description, but only by the appended claims.

We claim:

1. A system for monitoring a user, the system comprising:
a user-wearable sensor device configured to be directly or indirectly secured to the user or to an article worn by the user;
the user-wearable sensor device including at least one sensor configured to collect sensor data associated with an orientation of the user;
a display unit integral with the user-wearable sensor device and including at least one LED or other visual indicator; and
a data analysis system communicatively coupled with the at least one sensor and configured to analyze the user's orientation with respect to a turning protocol for the user, the data analyze system comprising a processor configured to:
receive sensor data collected by the at least one sensor;
analyze the sensor data to determine the orientation of the user; and
determine an amount of time that the user has spent in each of a plurality of different orientations:
wherein the display unit integral with the user-wearable sensor device is configured to display an indication of the determined amount of time that the user has spent in each of the plurality of different orientations.

2. The system of claim 1, wherein:
the processor of the data analysis system is configured to identify a particular orientation, from the plurality of different orientations, in which the user has spent the greatest amount of time; and
the display unit integral with the user-wearable sensor device is configured to display an indication of the identified orientation in which the user has spent the greatest amount of time.

3. The system of claim 1, wherein determining the amount of time that the user has spent in each of the plurality of different orientations comprises determining the amount of time that the user has spent in a current position during a period extending from a prior time to a current time.

4. The system of claim 1, wherein the display unit integral with the user-wearable sensor device is configured to indicate a current orientation of the user.

5. The system of claim 1, wherein the data analysis system is further configured to:
determine a compliance or non-compliance with a predefined turning protocol for the user; and
control the display unit to display information indicating the determined compliance or non-compliance with the predefined turning protocol.

6. The system of claim 1, wherein the data analysis system is further configured to:
determine when a change in the user's orientation is specified according to a predefined turning protocol; and
control the display unit to indicate the specified change in the user's orientation according to the predefined turning protocol.

7. A method of monitoring a user, the method comprising:
collecting, by at least one sensor of a user-worn sensor device directly or indirectly secured to a user or to an article worn by the user, sensor data associated with an orientation of the user;
monitoring, by a processor of the user-wearable sensor device, the orientation of the user over time with respect to a turning protocol for the user based on the sensor data collected by the at least one sensor;
receiving, the processor, sensor data collected by the at least one sensor;
analyzing, by the processor, the sensor data to determine the orientation of the user;

determining, by the processor, an amount of time spent in each of a plurality of different orientations based on the monitored orientation of the user over time;

displaying, via a display unit integral with the user-worn sensor device, information indicating a relative amount of time that the user has spent in the plurality of different orientations, wherein the display unit includes at least one LED or other visual indicator.

8. The method of claim 7, comprising:

identifying, by the processor, a particular orientation, from the plurality of different orientations, in which the user has spent the greatest amount of time; and displaying, via the display unit integral with the user-wearable sensor device, an indication of the identified orientation in which the user has spent the greatest amount of time.

9. The method of claim 7, wherein determining the amount of time spent in each of the plurality of different orientations comprises determining the amount of time spent in a current position during a period extending from a prior time to a current time.

10. The method of claim 7, comprising indicating, via the display unit integral with the user-wearable sensor device, a current orientation of the user.

11. The method of claim 7, further comprising:

determining a compliance or non-compliance with a predefined turning protocol for the user; and controlling the display unit to display information indicating the determined compliance or non-compliance with the predefined turning protocol.

12. The method of claim 7, further comprising:

determining when a change in the user's orientation is specified according to a predefined turning protocol; and controlling the display unit to indicate the specified change in the user's orientation according to the predefined turning protocol.

* * * * *